United States Patent [19]

Rickards et al.

[11] Patent Number: 4,703,127
[45] Date of Patent: Oct. 27, 1987

[54] PROCESS FOR THE PREPARATION OF PROSTANOIDS

[75] Inventors: Rodney W. Rickards, Weetangerra; Melvyn Gill, Hughes, both of Australia; Robert M. Christie, Neilston, Scotland

[73] Assignee: The Australian National University, Australian Capital Territory, Australia

[21] Appl. No.: 528,889

[22] Filed: Sep. 2, 1983

Related U.S. Application Data

[63] Continuation of Ser. No. 240,452, Mar. 4, 1981, abandoned, which is a continuation of Ser. No. 70,920, Aug. 30, 1972, abandoned.

[30] Foreign Application Priority Data

Sep. 4, 1978 [AU] Australia ............................ PD5809

[51] Int. Cl.⁴ ...................... C07D 309/12; C07F 7/04; C07C 69/67; C07C 29/00
[52] U.S. Cl. .................................. 549/214; 549/414; 549/415; 549/472; 549/473; 549/475; 556/429; 556/436; 556/441; 556/449; 556/482; 560/121; 560/122; 562/503; 562/504; 568/667; 568/446; 568/379; 568/62; 568/45
[58] Field of Search ................ 560/121, 122; 562/503, 562/504; 568/45, 62, 446, 379, 667; 556/429, 441, 436, 449, 482; 549/214, 414, 415, 472, 473, 475

[56] References Cited

U.S. PATENT DOCUMENTS

| | | | |
|---|---|---|---|
| 3,910,965 | 10/1975 | Sakai et al. | 560/122 |
| 4,031,129 | 6/1977 | Sih et al. | 549/414 |
| 4,107,181 | 8/1978 | Evans | 568/122 |
| 4,132,726 | 1/1979 | Kurozumi et al. | 568/667 |

OTHER PUBLICATIONS

Greene, Theodora W., "Protective Groups in Organic Synthesis", John Wiley & Sons, New York, 1981, pp. 10–50.

Primary Examiner—Nicky Chan
Attorney, Agent, or Firm—Bacon & Thomas

[57] ABSTRACT

Compounds of the general formula I are disclosed as useful intermediates in the preparation of prostanoids:

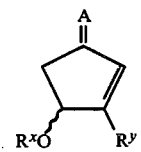

(wherein
  A represents O or H, OR$^z$;
  R$^z$ represents hydrogen or a protecting group;
  R$^x$ represents hydrogen or a protecting group; and
  R$^y$ represents halogen, a substituted thio group, disubstituted amino group, or a group of the formula R$^2$, and R$^2$ represents a straight- or branched-chain alkyl alkenyl or alkynyl group which may optionally be substituted by one or more carboxyl, carboxylic acid ester, or free or protected hydroxyl, thiol, aldehyde or keto groups;

with the provisos that R$^x$ is not hydrogen when A is O and R$^y$ is R$^2$; and that when A is H, OR$^z$ R$^y$ and R$^2$ and R$^x$ and R$^z$ are not both hydrogen.

Processes for the preparation of these compounds and of 2-substituted 4-hydroxy-cyclopent-2-en-1-one derivatives are also disclosed.

25 Claims, No Drawings

PROCESS FOR THE PREPARATION OF PROSTANOIDS

This application is a continuation of application Ser. No. 240,452, filed Mar. 4, 1981, which is a contnuation of Ser. No. 070,920 filed Aug. 30, 1979, both abandoned.

This invention relates to processes for the synthetic preparation of compounds of the prostaglandin group, including both naturally-occurring members and various modified analogues. These compounds are herein collectively termed prostanoids (E. J. Corey, T. Ravindranathan, and S. Terashima, *J. Am. Chem. Soc.*, 1971, 93, 4326).

Natural prostaglandins, exemplified by prostaglandin $E_1(14)$, are a family of biologically-active lipids which are normal constituents of animal and human tissues, or are elaborated by these tissues in response to various stimuli. Although present in very low concentrations, they are believed to be involved in a wide variety of biological processes, including reproduction, muscle expansion and contraction, respiration, lipid metabolism, kidney function, central nervous system activity, gastric secretion, cardiovascular activity, immune response, and temperature control. They have been the subject of extensive research and review. (See for example, P. Crabbé (ed.), "Prostaglandin Research", Academic Press, New York, 1977; K. H. Gibson, *Chem. Soc. Rev.*, 1977, 6, 489; N. Kharasch and J. Fried (eds), "Biochemical Aspects of Prostaglandins and Thromboxanes", Academic Press, New York, 1977). A number of routes are available for the synthesis of prostaglandins identical in structure and configuration with the natural materials. (See for example, A. Mitra, "The Synthesis of Prostaglandins", Wiley and Sons, New York, 1977; J. S. Bindra and R. Bindra, "Prostaglandin Synthesis", Academic Press, New York, 1977; P. Crabbé (ed), "Prostaglandin Research", Academic Press, New York, 1977).

Widespread therapeutic use of prostaglandins, derived either from natural sources or laboratory synthesis, has to date been hindered primarily by their rapid inactivation by metabolic processes in vivo and by their limited selectivity of action. Attempts to overcome these drawbacks have involved the synthesis of analogues with improved metabolic stability and improved selectivity compared to the natural compounds. (See for example, A. Mitra, "The Synthesis of Prostaglandins", Wiley and Sons, New York, 1977; J. S. Bindra and R. Bindra, "Prostaglandin Synthesis", Academic Press, New York, 1977; P. Crabbé (ed) "Prostaglandin Research", Academic Press, New York, 1977; D. Orth and H-E.Radunz, *Top. Curr. Chem.*, 1977, 72, 51). Variation of the two side chains which are attached to the cyclic prostaglandin nucleus has been a promising approach in this regard.

Several prostanoids of natural and modified structure currently find use in clinical and veterinary practice [K. B. Mallion, in "Aliphatic Chemistry", ed. A. McKillop (Specialist Periodical Reports), The Chemical Society, London, 1977, Vol. 5, p.240].

It is an object of the present invention to provide an improved process for the preparation of prostanoids and novel intermediates prepared therein.

The conversion of 2-substituted 4-hydroxycyclopent-2-en-1-one derivatives of the formula :

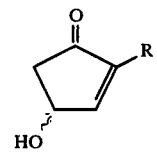

into prostanoids by means of conjugate addition reactions has been previously described. (See for example, G. Stork and T. Takahashi, *J. Am. Chem. Soc.*, 1977, 99 1275; C. J. Sih, J. B. Heather, R. Sood, P. Price, G. Peruzzotti, L. F. H. Lee and S. S. Lee, *J. Am. Chem. Soc.*, 1975, 97, 865; C. J. Sih, R. G. Salomon, P. Price, R. Sood and G. Peruzzotti, *J. Am. Chem. Soc.*, 1975, 97, 857; F. S. Alvarez, D. Wren, and A. Price, *J. Am. Chem. Soc.*, 1972, 94, 7823; A. F. Kluge, K. G. Untch and J. H. Fried, *J. Am. Chem. Soc.*, 1972, 94, 7827; A. F. Kluge, K. G. Untch, and J. H. Fried, *J. Am. Chem. Soc.*, 1972, 94, 9256). By these conjugate addition reactions, either natural prostaglandins or a wide range of modified analogues thereof may be prepared. It is a particular object of the present invention to provide an improved process for the preparation of 2-substituted 4-hydroxycyclopent-2-en-1-one derivatives of the above type, whereby a convenient and efficient process for the preparation of prostanoids is provided enabling ready access to the prostanoids either as optically pure stereoisomers or as mixtures thereof. The preparation from common intermediate compounds of either natural prostaglandins or a wide range of modified analogues thereof, is thus facilitated, According to a first aspect of the present invention there are provided, as novel intermediates in the production of prostanoids, compounds of the general formula I:

wherein A represents O or H,$OR^z$; $R^z$ represents hydrogen or a protecting group; $R^x$ represents hydrogen or a protecting group; and $R^y$ represents halogen, particularly chlorine, bromine or iodine, a substituted thio group, particularly an alkyl thio group, a di-substituted amino group, particularly a di-alkyl amino group, or a group of the formula $R^2$, and $R^2$ represents a straight- or branched-chain alkyl,alkenyl or alkynyl group for example of up to 10 carbon atoms, particularly of 4 to 10 carbon atoms, which may optionally be substituted by one or more carboxyl, carboxylic acid ester, or free or protected hydroxyl, thiol, aldehyde or keto groups; with the provisos that $R^x$ is not hydrogen when A is O and $R^y$ is $R^2$; and that when A is H,$OR^z$, $R^y$ is $R^2$, and $R^x$ and $R^z$ are not both hydrogen.

As used throughout this specification, the term "protecting group" is used to denote a removable protective group for an alcoholic hydroxyl group. Such groups are well known and include, for example, substituted silyl groups, alkoxyalkyl groups, a tetrahydrofuran-2-yl group and a tetrahydropyran-2-yl group.

Preferably, the protecting group represented by $R^z$ is an alkoxyalkyl group such as an ethoxyethyl group, a tetrahydrofuran-2-yl group or a tetrahydropyran2-yl group. Preferably also, the protecting group represented by $R^x$ is a silyl group tri-substituted with alkyl and/or aryl residues, for example, a dimethyl-t-butylsilyl group.

The carboxylic acid ester groups which may be optional substituents on the $R^2$ chain include, for example, the lower alkyl esters. The protected hydroxy or thiol groups which similarly may be optional substituents include ethers and their thio analogues for example, lower alkyl ethers and thio-ethers and hydroxy groups protected with protecting groups such as substituted silyl groups, alkoxyalkyl groups, a tetrahydrofuran-2-yl group or a tetrahydropyran-2-yl group. The protected aldehyde or keto groups which may also be optional substituents include non-cyclic and cyclic acetals or ketals and their thio analogues.

According to a further aspect of this invention there is provided a process for the preparation of compounds of the general formula I as defined above wherein A represents O, which comprises :

(a) partial dehalogenation of a compound of the general formula II :

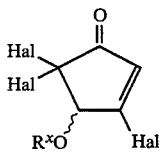

wherein Hal represents halogen and $R^x$ is as defined above, to produce a compound of the general formula Ia:

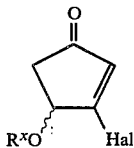

wherein Hal and $R^x$ are as defined above; and, if desired, total or partial inversion of the hydroxyl or protected hydroxyl substituent;

(b) protection of the hydroxyl substituent of a compound of the general formula Ia as defined above in which $R^x$ represents hydrogen to produce a compound of the general formula Ib:

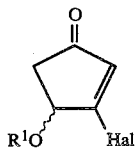

wherein Hal is as defined above and $R^I$ represents a protecting group; and, if desired, total or partial inversion of the protected hydroxyl substituent;

(c) replacement of the halogen substituent of a compound of the general formula Ib as defined above, to produce a compound of the general formula Ic:

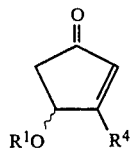

wherein $R^4$ represents a substituted thio group or a disubstituted amino group and $R^I$ represents a protecting group; and, if desired, total or partial inversion of the protected hydroxyl substituent; and (d) reaction of a compound of the general formula Ib as defined above or of a compound of the general formula Ic as defined above in a conjugate addition-elimination reaction to produce a compound of the general formula Id:

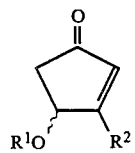

wherein $R^I$ represents a protecting group and $R^2$ is as defined above, and, if desired, total or partial inversion of the protected hydroxyl substituent.

Preferably, said compound of the general formula II is prepared by oxidative decarboxylation of a compound of the general formula IIa:

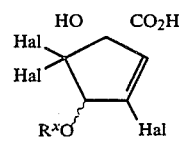

wherein Hal represents a halogen and $R^x$ is as defined in claim 1; if desired, protection of the hydroxyl substituent of a compound of the general formula IIa in which $R^x$ represents hydrogen; and, if desired, total or partial invertion of the hydroxyl or protected hydroxyl substituent.

Preferably also, said compound of the general formula IIa is prepared by ring-contraction of phenol or 2,4,6-trihalophenol with a halogen in the presence of an alkali.

If desired, the process of this aspect may also include the step of total or partial resolution of a racemic mixture of a compound of the general formula Ia, Ib, Ic, Id, II or IIa. In addition, the process may also include the step of modification of the group represented by $R^2$ or of addition, replacement or modification of an optional substituent on the group represented by $R^2$ in a compound of the general formula Id.

According to a further aspect of this invention, there is provided a process for the preparation of compounds of the general formula I as defined above wherein A represents H, $OR^z$ and $R^y$ represents $R^2$, which comprises :

(a) reduction of a compound of the general formula Id :

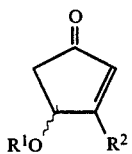
Id $R^1$ represents a protecting group and $R^2$ is wherein R as defined above to produce a compound of the general formula Ie

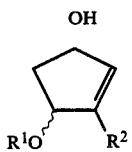
Ie wherein $R^1$ represents a protecting group and $R^2$ is as defined above; and if desired, total or partial inversion of the configuration of the hydroxyl substituent;

(b) protection of the free hydroxyl substituent of a compound of the general formula Ie as defined above to produce a compound of the general formula If

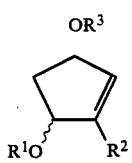
If wherein $R^1$ represents a protecting group, $R^3$ represents a protecting group and $R^2$ is as defined above; and if desired, total or partial inversion of the configuration of the —$OR^3$ substituent; and (c) selective removal of the $R^1$ protecting group of a compound of the general formula If as defined above to produce a compound of the general formula Ig

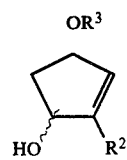
Ig wherein $R^3$ represents a protecting group and $R^2$ is as defined above; and, if desired, total or partial inversion of the configuration of the —$OR^3$ substituent.

The process of this aspect may also include the step of total or partial resolution of a racemic mixture of the compound of the general formula Ie, If or Ig. In addition, the process may also include the step of modification of the group represented by $R^2$ in a compound of the general formula Ie, If or Ig.

According to yet another aspect of this invention, there is provided a process for the preparation of compounds of the general formula III:

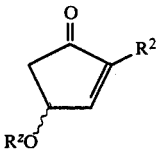
III wherein $R^2$ represents a straight- or branched-chain alkyl, alkenyl or alkynyl group which may optionally be substituted by one or more carboxyl, carboxylic acid ester, or free or protected hydroxy, thiol, aldehyde or keto groups; and $R^z$ represents hydrogen or a protecting group; which comprises:

(a) when $R^z$ represents a protecting group, oxidation of the free hydroxyl group of a compound of the general formula Ig:

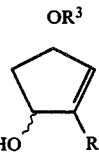
Ig wherein $R^3$ represents a protecting group and $R^2$ is as defined above, to produce a compound of the general formula IIIa:

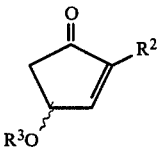
IIIa wherein $R^3$ represents a protecting group and $R^2$ is as defined above; and if desired, total or partial inversion of the configuration of the protected hydroxyl substituent; and (b) when $R^z$ represents hydrogen, removal of the protecting group of a compound of the general formula IIIa as defined above, to produce a compound of the general formula IIIb:

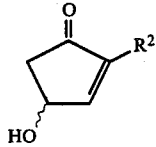
IIIb wherein $R^2$ is as defined above; and, if desired, total or partial inversion of the configuration of the hydroxyl substituent.

It is a particular feature of the present invention that the partial dehalogenation of the compounds of formula II leads to compounds of formulae Ib and Ic, which undergo highly efficient additionelimination reactions to form the compounds of formula Id.

As noted above, prostanoids have been prepared from compounds of the general formula III and, if desired, the $R^z$ protecting group may be removed or replaced by an alternative protecting group prior to conversion of the compounds of general formula III into prostanoids.

It will be appreciated that the various compounds referred to throughout this specification are chiral and the present invention relates both to the individual stereoisomers and to any mixtures thereof whether these mixtures include enantiomers and/or diastereoisomers. In accordance with accepted nomenclature, the dotted lines used in the formulae throughout this specification indicate that the attached group lies behind the general plane of the ring system, i.e., that the group is in an α-configuration; whilst thickened lines indicate that the attached group lies in front of the general plane of the system, i.e., that the group is in a β-configuration. The wavy lines used in the formulae throughout this specification indicate that the attached group is present in an α- or β-configuration or is present in both α- and β-configurations, thus including not only all the individual stereoisomers thereof, but also all mixtures of such stereoisomers, including optically inactive racemic mixtures of enantiomers and optically active mixtures in which one enantiomer is present in excess relative to the other enantiomer, as well as mixtures of diastereoisomers.

It will be appreciated from the above general description and from the further description hereinafter that the present invention provides several advantages including :

(i) the ready accessibility of prostanoids either as optically pure stereoisomers or as mixtures thereof;

(ii) the preparation from common intermediates of either natural prostaglandins or a wide range of modified analogues;

(iii) the preparation of the common intermediates for the synthesis of prostanoids from a cheap, readily available starting material;

(iv) processes which are convenient to carry out and efficient in their synthetic yields;

(v) processes which permit the facile introduction of isotopic labels in certain stages, the resulting labelled prostanoids being of value in biological studies.

Formulae (1) to (20) referred to in the following detailed description of preferred processes and compounds of the present invention are set out on the following pages.

Both naturally-occurring prostaglandins and modified analogues, collectively termed prostanoids, can be prepared from the known racemic (1R*, 4R*)-3,5,5-trichloro-1,4-dihydroxycyclopent 2-ene-1-carboxylic acid (3) (R. M. Christie, R. W. Rickards, K. J. Schmalzl and D. Taylor, Aust.J.Chem., 1977, 30, 2195; A. W. Burgstahler, T. B. Lewis, and M. O Abdel-Rahman, J. Org. Chem., 1966, 31, 3516; C. J. Moye and S. Sternhell, Aust. J. Chem., 1966, 19, 2107). This acid (3) can itself be prepared from phenol (1) or 2,4,6-trichlorophenol (2) by the known reaction involving ring-contraction with chlorine in the presence of an alkali.

For the preparation of racemic prostanoids, the racemic acid (3) can be used as such without resolution into its enantiomers. For the preparation of stereochemically pure prostanoids, the racemic acid (3) can be resolved into its enantiomers (4) and (5) by suitable methods known in the art, for example by the use of an optically active base which yields separable diastereoisomeric salts from which the two enantiomeric acids (4) and (5) may be recovered. Alternatively, for the preparation of stereochemically pure prostanoids, the racemic acid (3) may be used and a racemic compound produced from it in the synthetic sequence may be totally resolved into its individual enantiomers. Partial resolution at any stage will produce mixtures in which one enantiomer is present in excess relative to the other.

The process leading to stereochemically pure prostanoids will be described in detail for the resolved enantiomer (4) of the racemic acid (3). It will be clear to people skilled in the art, however, that resolution may be effected at a later stage, or that the process may be carried out with partial or no resolution.

(1)

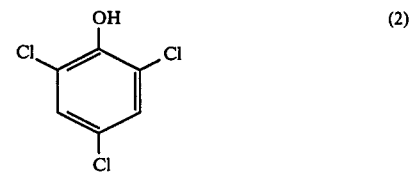

(2)

(3)

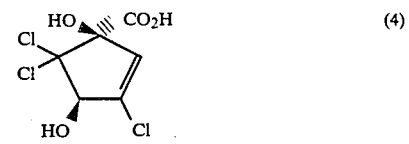

(4)

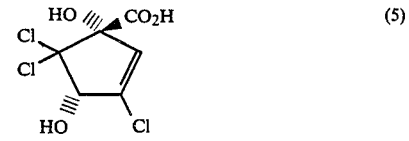

(5)

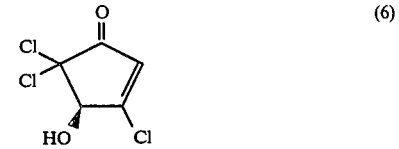

(6)

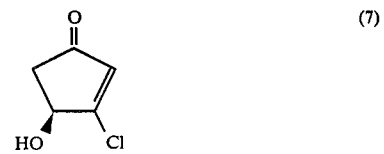

(7)

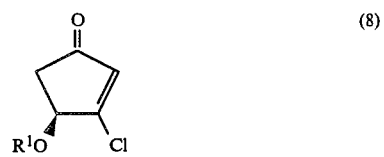

(8)

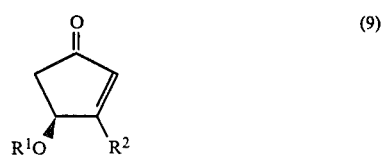

(9)

-continued

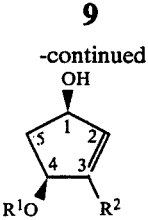 (10)

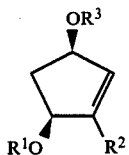 (11)

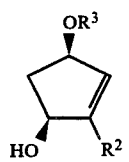 (12)

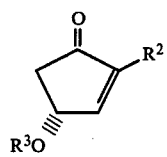 (13)

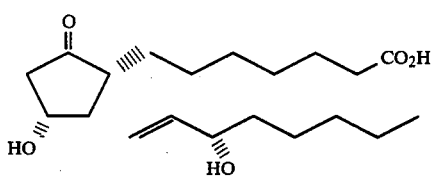 (14)

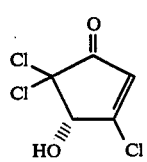 (15)

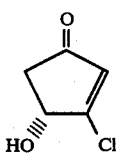 (16)

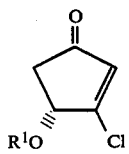 (17)

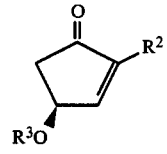 (18)

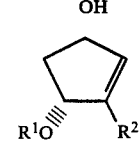 (19)

-continued

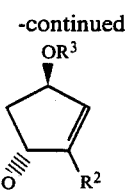 (20)

Oxidative decarboxylation of the (1R, 4R)-enantiomer (4) of the racemic acid (3) yields the (4R)-3,5,5,-trichloro-4-hydroxycyclopent-2-en-1-one (6), this reaction being known in the literature for the corresponding racemic compounds (R. Effenberger and R. W. Rickards, Aust. J. Chem., 1975, 28, 2731). The trichloroenone (6) can be partially dechlorinated by certain reducing agents to (4S)-3-chloro-4-hydroxycyclopent-2-en-1-one (7). Protection of the hydroxyl function of the chloro-enone (7) with a suitable group $R^I$, which is stable to the ensuing reaction conditions but which can be selectively removed when necessary, yields derivatives (8) of (4S)-3-chloro-4-hydroxycyclopent-2-en-1-one which are versatile synthetic intermediates.

These chloro-enone derivatives (8), or the corresponding compounds resulting from replacement of the 3-chloro substituent by a different halogen or a substituted thio or di-substituted amino group, undergo facile conjugate addition-elimination reactions with certain organometallic species. Copper-mediated reactions involving organomagnesium or organolithium reagents are particularly efficient for this step. The products are derivatives (9) of 3-substituted (4S)-4-hydroxycyclopent-2en-1-ones, in which $R^2$ is an alkyl, alkenyl, alkynyl or otherwise functionalised alkyl substituent derived from the organometallic reagent, and in which the functionality is compatible both with this step and with subsequent steps.

Stereospecific reduction of the 1.-carbonyl function in these 3-substituted enones (9) for example with a suitable metal hydride, gives derivatives (10) of 3-substituted (1R, 4S)-cyclopent-2-en-1,4-diols in which the 1- and 4- substituents have cis relative stereochemistry and in which the 4-hydroxyl function remains protected. Protection of the newly-formed 1-hydroxyl function of the alcohols (10) with a suitable group $R^3$ which is stable to the ensuing reaction conditions but which can be selectively removed when necessary, yields derivatives (11) of 2-substituted (1S, 4R)-cyclopent-2-en-1,4-diols in which both the 1-and 4-hydroxyl substituents are now protected. [Note that IUPAC Nomenclature Rules require a change of numbering in derivatives of type (11) compared to those of type (10)].

Selective removal of the $R^1$ protecting group from the 1-hydroxyl function of these diol derivatives (11) yields derivatives (12) of 2-substituted (1S, 4R)-cyclopent -2-en-1,4-diols in which the 4-hydroxyl function only is now protected. Oxidation of the 1-hydroxyl function in these alcohols (12) gives derivatives (13) of 2-substituted (4R)-4-hydroxy-cyclopent-2-en-1-ones, in which the 4-hydroxyl function is still protected.

2-substituted (4R)-4-hydroxycyclopent-2-en-1-one derivatives of type (13) have previously been converted into prostanoids via conjugate addition reactions (C. J. Sih, J. B. Heather, R. Sood, P. Price, G. Peruzzotti, L. F. H. Lee & S. S. Lee, J. Am. Chem. Soc., 1975,97,865; G. Stork and T. Takahashi, J. Am. Chem. Soc., 1977, 99, 1275). Alternatively, the $R^3$ protecting group can be removed from the 4-hydroxyl function of these derivatives (13) and replaced by an alternative protecting group prior to conversion into prostanoids.

The substituent $R^2$ in the derivatives (9) of 3-substituted (4S)-4-hydroxycyclopent-2-en-1-ones may, as stated above, be an alkyl, alkenyl, alkynyl or otherwise functionalised alkyl substituent. Its functionality is initially limited by the requirement for compatibility with the organometallic process by which it is introduced. This substituent $R^2$ may if desired, however, be modified subsequent to its introduction. Such modification may be carried out either on the 3-substituted enones (9) or at any appropriate later stage or stages in the sequence from these 3-substituted enones (9) through the substituted cyclopentenes (10), (11) and (12) to the 2-substituted (4R)-4-hydroxycyclopent-2-en-1-one derivatives of type (13). The carbon chain itself may be modified, or optional substituents in it may be added, replaced, or modified. It will be understood that such reactions carried out on the side-chain must be compatible with the structural features of the particular nucleus of type (9), (10), (11), (12) or (13) to which it is attached, and the resulting modified $R^2$ side-chain must itself be compatible with any subsequent process carried out.

If the (1S, 4S)-enantiomer (5) of the racemic acid (3) is subjected to a similar sequence of reactions to that described above, the derivatives (18) of 2-substituted (4S)-4-hydroxycyclopent-2-en-1-ones result, which are enantiomeric to the 2-substituted (4R)-4-hydroxycyclopent-2-en-1-one derivatives of type (13). However, (4R)-derivatives of type (13) can also be prepared from the (1S, 4S)-enantiomer (5) of the racemic acid (3) by carrying out an inversion of configuration. It will be appreciated that this inversion may be effected at any appropriate stage of the synthesis, and that only one such inversion is necessary even though some of the intermediates contain two chiral centres. For example, inversion of the configuration of the hydroxyl function in the derivatives (19) of the 3-substituted (1S, 4R)-cyclopent-2-en-1,4-diols yields derivatives (20; $R^3$=H) of 3-substituted (1R, 4R)-cyclopent-2-en-1,4-diols in which the ring oxygen functions are now trans- rather than cis-related related. Bimolecular nucleophilic substitution reactions are suitable for this inversion. Subsequent reaction steps similar to those carried out on the cis-derivatives (10) then lead, via destruction of the non-inverted chiral centre, to the 2-substituted (4R)-4-hydroxycyclopent-2-en-1-one derivatives of type (13). (In the detailed Examples which follow, this inversion of configuration is illustrated on racemic material, since the change in relative stereochemistry is sufficient to establish that inversion has occurred).

Furthermore, the nature of the processes described permits the preparation of prostanoids which are isotopically labelled at specific sites. Such labelled compounds are of value in biological studies of prostanoids and their metabolites, in which various techniques are employed such as radioactive assay, radioimmunoassay, mass spectroscopy and coupled gas chromatography-mass spectroscopy. (See for example, B. Samuelsson, E. Granström, K. Green, M. Hamberg, and S. Hammarström, *Ann. Rev. Biochem.*, 1975, 44, 669). Appropriate isotopic labels include deuterium or tritium, and/or carbon-13 or carbon-14. These labelled atoms can be introduced at various stages of the processes described by employing an appropriate isotopically labelled substrate and/or an isotopically labelled reagent.

For example, the 2-substituted (4R)-4-hydroxycyclopent-2-en-1-one derivatives (13) may be prepared labelled with $^{14}C$ in all carbon atoms of the cyclopentenone ring by using [U-$^{14}C$] phenol as a starting material for the above process, or specifically labelled in the $R^2$-side chain by use of the corresponding labelled organometallic species in the conjugate addition-elimination reaction which converts the chloro-enones (8) into the 3-substituted enones (9). Alternatively, the 2-substituted (4R)-4-hydroxycyclopent-2-en-1-one derivatives (13) may be labelled with deuterium or tritium at C-5 of the cyclopentenone ring by using isotopic proton sources (e.g. deuterium oxide, or tritiated alcohols) in the reduction of the trichloro-enone (6) to the chloro-enone (7), or at C-4 of the ring by use of deuterated or tritiated metal hydrides for the reduction of the 3-substituted enones (9) to the alcohols (10). Labelled prostanoids may then be prepared from such labelled 2-substituted (4R)-4-hydroxycyclopent-2-en-1-one derivatives (13).

Specific details of the compounds of the present invention and the reactions involved in the processes of this invention are illustrated by the following detailed examples. In these examples, all temperatures are in degrees Centigrade, and technical terms (e.g. chromatography, etc.,) have the usual meaning in the art. Crude reaction products can be purified by the means described herein, or by other means known in the art.

EXAMPLE 1

(1R,4R)-3,5,5-Trichloro-1,4-dihydroxycyclopent-2-ene-1-carboxylic acid (4).

To ($\pm$)-3,5,5-trichloro-1,4-dihydroxycyclopent-2-ene-1-carboxylic acid (3) (A. W. Burgstahler, T. B. Lewis, and M. O. Abdel-Rahman, *J. Org. Chem.*, 1966, 31, 3516; C. J. Moye and S. Sternhell, *Aust. J. Chem.*, 1966 19, 2017) (10 g, 40.4 mmol) in methanol (1l) was added ($-$)-brucine (15.94 g, 40.4 mmol) in methanol (1l). Crystallisation at room temperature gave two crops (8.50 and 2.33 g respectively) of relatively pure ($-$)-brucine salt of the acid (4), $[\alpha]_D^{25}$- 110° (c 0.24, CHCl$_3$). Recrystallisation from methanol gave the pure ($-$)-brucine salt of the acid (4) (9.64 g, 74%) as colourless plates, m.p. 143°–146°, $[\alpha]_D^{25}$ $-120°$ (c 0.247, CHCl$_3$ ) (Found : C, 54.1; H, 4.85; Cl, 16.4; N, 4.05. C$_{29}$H$_{31}$Cl$_3$N$_2$O$_8$ requires C, 54.25; H, 4.85; Cl 16.55; N, 4.35%).

0.5M-Hydrochloric acid (60 ml) was added to a suspension of the ($-$)-brucine salt of the acid (4) (5.6 g, 8.72 mmol) in ether (50 ml), and the mixture shaken until the salt had dissolved. The aqueous phase was separated, extracted with ether (6×25 ml), and the combined ether solutions were washed successively with 0.11M-hydrochloric acid (20 ml) and saturated aqueous sodium chloride (2×15 ml) before drying (MgSO$_4$). Evaporation of the ether under reduced pressure gave the (1R, 4R)-acid (4) (2.03 g, 94%) as colourless rhombs from ether-light petroleum (b.p. 40°–60°),m.p.188°–190°, $[\alpha]_D^{25}$ $-207°$(c 0.100, EtOH ), $[\alpha]_{232}^{25}-15,060°$ (c 5.18×10$^{-3}$, EtOH), $[\theta]_{219}^{25}-75,490°$(c. 5.18×10$^{-3}$, EtOH) (Found: C, 29.35; H, 1.95; Cl, 42.9.C$_6$H$_5$Cl$_3$O$_4$ requires C, 29.1; H,2.05; Cl, 43.0%).

EXAMPLE 2

(4R)-3,5,5-Trichloro-4-hydroxycyclopent-2-en-1-one (6)

The (1R,4R)-acid (4) (200 mg, 0.8 mmol) was added portionwise over 10 min to lead tetraacetate (500 mg, 1.13 mmol) in acetic acid (5 ml) containing water (0.05 ml) at 80°. After a further 5 min, water (25 ml) was added and the cooled mixture extracted with ether (3×25 ml). The combined ether solutions were extracted with 5% aqueous sodium bicarbonate until the washings were alkaline (pH 7.5–8), then washed with water (10 ml), dried (MgSO$_4$), and evaporated under reduced pressure. Short path distillation (bath temp. 60°/0.1 mmHg) gave the (4R)-enone (6) (160 mg, 98%) as a colourless oil, $[\alpha]_{357}^{25} +1547°$ (c 5.66×10$^{-2}$, EtOH) $[\alpha]_{252}^{25} -11,280°$ (c 2.26×10$^{-3}$, EtOH), $[\theta]_{333}^{25} +8407°$ (c. 5.66×10$^{-2}$,EtOH), $[\theta]_{240}^{25} -45,025°$ (c 2.26×10$^{-3}$, EtOH) (Found : C, 29.8; H, 1,65; Cl, 51.3; C$_5$H$_3$Cl$_3$O$_2$ requires C, 29.8; H, 1.5; Cl, 52.8%).

EXAMPLE 3

(4S)-3-Chloro-4-hydroxycyclopent-2-en-1-one (7)

To the (4R)-trichloro-enone (6) (325 mg, 1.61 mmol) in acetone (8 ml) at 0° and under carbon dioxide was added an aqueous solution (15 ml) of chromium (II) chloride (J. R. Hanson, *Synthesis*, 1974, 1; G. Rosenkranz, O. Mancera, J. Gatica, and C. Djerassi, *J. Am. Chem. Soc.* 1950, 72, 4077) at 0°. After 15 min the solution was extracted with ether (3×30 ml), and the combined extracts were evaporated under reduced pressure. The residue was dissolved in ether (30 ml), dried (MgSO$_4$) and evaporated to yield the crude (4S)-enone (7) (247 mg) as a thermally unstable oil. This crude product showed similar behaviour on thin layer chromatography (silica gel, methylene dichloride-methanol, 10:1) to the purified, fully characterised racemic material, and was used without further purification.

EXAMPLE 4

(4S)-3-Chloro-4-(dimethyl-t-butylsilyloxy)cyclopent-2-en-1-one (8; R$^1$=Me$_2$Bu$^t$Si)

Chlorodimethyl-t-butylsilane (485 mg, 3.22 mmol) was added over 5 min to the crude (4S)-enone (7) (247 mg) in hexamethylphosphoric triamide (2 ml) at 0°. After stirring at 4° for 20 h the solution was diluted with water (10 ml) and extracted with ether (3×10 ml). The combined ether extracts were washed with water (3×10 ml), dried (MgSO$_4$) and evaporated to give a pale yellow oil (456 mg) which was chromatographed on a column of silica gel (25 g) with methylene dichloride-methanol (50:1) as eluant. The (4S)-enone (8; R$^1$=Me$_2$Bu$^t$Si) [243 mg, 61% from the 3,5,5-trichloro-4-hydroxycyclopent-2-en-1-one (6)] was obtained as a colourless oil, $[\alpha]_{352}^{25} +1050°$ (c. 9.14×10$^{-2}$, hexane), $[\alpha]_{234}^{25} -16,140°$ (c 1.83×10$^{-3}$, hexane), $[\theta]_{333}^{25} +6700°$ (c 9.14×10$^{-2}$, hexane), $[\theta]_{222}^{25} -80,330°$ (c 1.83 ×10$^{-3}$, hexane]. (Found: C, 53.65; H, 7.95; Cl, 14.6. C$_{11}$H$_{19}$ClO$_2$Si requires C, 53.55; H, 7.75; Cl, 14.35%)

EXAMPLE 5

(4S)-4-(Dimethyl-t-butylsilyloxy)-3-[7-(dimethyl-t-butylsilyloxy) heptyl]-cyclopent-2-en-1-one (9; R$^1$=Me$_2$Bu$^t$Si, R$^2$=(CH$_2$)$_7$OSiMe$_2$Bu$^t$)

A suspension of cuprous iodide (64 mg, 0.326 mmol) in tetrahydrofuran (2 ml) containing the (4S)-enone (8; R$^1$=Me$_2$Bu$^t$Si) (80 mg, 0.326 mmol) was stirred vigorously at -10° under argon. Dropwise addition of 7-(dimethyl-t-butylsilyloxy)heptyl magnesium bromide in tetrahydrofuran (0.62 M, 1.0 ml, 0.620 mmol) produced a green solution which was stirred at -10° for 10 min. The reaction was rapidly quenched with saturated aqueous ammonium chloride (5 ml), and after the addition of ether (5 ml) the mixture was stirred at room temperature for 1 h before dilution with water (10 ml) and extraction with ether (5×10 ml). The combined extracts were washed with brine (2×5 ml), dried (MgSO$_4$) and evaporated. Purification by preparative layer chromatography on silica gel in methylene dichloridemethanol (50:1) gave the (4S)-enone (9; R$^1$=Me$_2$Bu$^t$Si, R$^2$=(CH$_2$)$_7$OSiMe$_2$Bu$^t$) (127 mg, 89%) as a colourless oil, $[\alpha]_{362}^{25} +781°$, $[\alpha]_{346}^{25} +781°$ (c 1.665×10$^{-2}$, hexane), $[\alpha]_{228}^{25} -11,110°$ (c 1.665×10$^{-3}$, hexane), $[\theta]_{326}^{25} +8538°$ (c 1.665×10$^{-2}$, hexane), $[\theta]_{217}^{25} -95,970°$ (c 1.665×10$^{-3}$, hexane)(Found: C, 65.55; H, 11.05. C$_{24}$H$_{48}$O$_3$Si$_2$ requires C, 65.4; H, 11.0%).

EXAMPLE 6

(1R,4S)-4-(Dimethyl-t-butylsilyloxy)-3-[7-(dimethyl-t-butylsilyloxy) heptyl]-cyclopent-2-en-1-ol (10; R$^1$=Me$_2$Bu$^t$Si, R$^2$=(CH$_2$)$_7$OSiMe$_2$Bu$^t$)

Lithium tri-s-butylborohydride in tetrahydrofuran (lM, 1.6 ml, 1.6 mmol) was added dropwise with vigorous stirring to the (4S)-enone (9; R$^1$=Me$_2$Bu$^t$Si, R$^2$=CH$_2$)$_7$OSiMe$_2$Bu$^t$)(350 mg, 0.79 mmol) in tetrahydrofuran (3 ml) at −78°. After 3 h at this temperature water (1 ml) was added and the mixture allowed to warm to room temperature. Dilution with water (10 ml) and extraction with ether (4×10 ml) gave, after drying (MgSO$_4$) and evaporation of the extracts, a pale yellow oil (690 mg). Preparative layer chromatography on silica gel in methylene dichloride-methanol (20:1) yielded the (1R,4S)-alcohol (10; R$^1$=Me$_2$Bu$^t$Si, R$^2$=(CH$_2$)$_7$OSiMe$_2$Bu$^t$) (287 mg, 82%) as a colourless oil. (Found: C 65.4; H, 10.95. C$_{24}$H$_{50}$O$_3$Si$_2$ requires C, 65.1; H, 11.4%).

EXAMPLE 7

(1S,4R)-1-(Dimethyl-t-butylsilyloxy)-2-[7-(dimethyl-t-butylsilyloxy) heptyl]-4-(tetrahydropyran-2-yloxy) cyclopent-2-ene (11; R$^1$=Me$_2$Bu$^t$Si, R$^2$=(CH$_2$)$_7$OSiMe$_2$Bu$^t$, R$^3$=Thp).

Dihydropyran (45.9 mg, 0.546 mmol) was added dropwise to the (1R,4S)-alcohol (10; R$^1$=Me$_2$Bu$^t$Si, R$^2$=(CH$_2$)$_7$OSiMe$_2$Bu$^t$) (220 mg, 0.497 mmol) in methylene dichloride (4 ml) containing p-toluenesulphonic acid (0.01 M) at 0°. After 3 hr. the solution was diluted with ether (15 ml), washed successively with 5% aqueous sodium bicarbonate (5 ml) and water (2×5 ml), and then dried (MgSO$_4$). Removal of the solvent under reduced pressure and chromatography of the residue on a column of silica gel (30 g) in methylene dichloride-methanol (50:1) gave the (1S,4R)-diol derivative (11; R$^1$=Me$_2$Bu$^t$Si, R$^2$=(CH$_2$)$_7$OSiMe$_2$Bu$^t$, R$^3$=Thp) (197 mg, 75%) as a colourless oil. (Found: C,66.4; H, 11.1. C$_{29}$H$_{58}$O$_4$Si$_2$ requires C, 66.1; H, 11.1%).

EXAMPLE 8

(1S,4R)-2-(7-Hydroxyheptyl)-4-(tetrahydropyran-2-yloxy)cyclopent-2-en-1-ol (12; R$^{R3}$=Thp)

To the (1S,4R)-diol derivative (11; R$^1$=Me$_2$Bu$^t$Si, R$^2$=(CH$_2$)$_7$OSiMe$_2$Bu$^t$, R$^3$=Thp) (174 mg, 0.33 mmol) in tetrahydrofuran (3 ml) at 0° was added slowly tetrabutylammonium flouride in tetrahydrofuran (0.4 M, 4 ml). After 4h at 0° the solution was diluted with water (5 ml) and extracted three times with ether (20 ml, $2\times10$ ml). The combined extracts were washed with saturated brine ($2\times10$ ml), dried ($MgSO_4$), and evaporated. Chromatography of the residual oil on a column of silica gel (7g) in methylene dichloridemethanol (10:1) gave the (1S,4R)-diol (12; $R^2=(CH_2)_7OH$, $R^3=Thp$) (92 mg, 93%) as a colourless oil (Found: C,68.6; H,10.0. $C_{17}H_{30}O_4$ requires C, 68.4; H, 10.15%).

EXAMPLE 9

(4R)-2-(6-Carboxyhexyl)-4-(tetrahydropyran-2-yloxy) cyclopent-2-en-1-one* (13; $R^2=(CH_2)_6CO_2H$, $R^3=Thp$)

Jones reagent (K. Bowden, I. M. Heilbron, E. R. H. Jones, and B. C. L. Weedon, *J. Chem. Soc.*, 1946,39) was added over 2.5 h to the (1S,4R)-diol (12; $R^2=(CH_2)_7OH$, $R^3=Thp$) (74 mg, 0.248 mmol) in acetone (6 ml) at $-20°$ so that an excess of oxidant was maintained. After a further 30 min isopropanol was added to destroy excess of oxidant. The solution was diluted with water (10 ml), extracted with ether ($5\times10$ ml), and the combined extracts were washed with saturated brine ($3\times5$ ml), dried ($MgSO_4$), and evaporated under reduced pressure. The (4R)-acid (13; $R^2=(CH_2)_6CO_2H$, $R^3=Thp$) (75 mg) was obtained as a chromatographically pure oil (Found: M+, 310.1780. $C_{17}H_{26}O_5$ requires M, 310.1780).(* This compound is named here as a substituted ketone rather than as a substituted carboxylic acid, so as not to obscure the description).

EXAMPLE 10

(4R)-2-(6-Methoxycarbonylhexyl)-4-(tetrahydropyran-2-yloxy)cyclopent-2-en-1-one** (13; $R^2=(CH_2)_6CO_2Me$, $R^3=Thp$)

An excess of ethereal diazomethane was added to the chromatographically pure (4R)-acid (13; $R^2=(CH_2)_6CO_2H$, $R^3=Thp$) (75 mg) in ether (10 ml). After 30 min the excess of reagent was destroyed by dropwise addition of acetic acid, and the resulting ethereal solution was washed successively with 5% aqueous sodium bicarbonate (5 ml) and water ($2\times5$ ml) before drying ($MgSO_4$). Removal of the ether under reduced pressure and preparative layer chromatography of the residual oil on silica gel in methylene dichloride-methanol (20:1) afforded the (4R)-ester (13; $R^2=(CH_2)_6CO_2Me$, $R^3=Thp$) [67 mg, 83% from the (1S,4R)-diol (12; $R^2=(CH_2)_7OH$, $R^3=Thp$)] as a colourless oil, $[\alpha]_{341}^{25}-1482°$ (c $4.47\times10^{-2}$, MeOH), $[\alpha]_{238}^{25}+10,510°$ (c $4.47\times10^{-3}$, MeOH), $[\alpha]_{323}^{25}-11,305°$ (c $4.47\times10^{-2}$, MeOH), $[\theta]_{226}^{25}+63,785°$ (c $4.47\times10^{-3}$, MeOH) (Found: C, 66.35; H,8.6.$C_{18}H_{28}O_5$ requires C, 66,65; H,8.7%). (** This compound is named here as a substituted ketone rather than as a substituted ester, so as not to obscure the description.)

EXAMPLE 11

(4R)-4-Hydroxy-2-(6-methoxycarbonylhexyl)cyclopent-2-en-1-one* (13; $R^2=(CH_2)_6CO_2Me$, $R^3=H$)

The (4R)-ester (13; $R^2=(CH_2)_6CO_2Me$. $R^3=Thp$) (40 mg, 0.123 mmol) in acetic acid-tetrahydrofuran-water (3:1:1, 2 ml) was maintained at room temperature for 24 h. Solvent was removed under reduced pressure, and the residue, dissolved in ethyl acetate (10 ml), was washed successively with 5% aqueous sodium bicarbonate (5 ml) and saturated brine ($2\times5$ ml). After drying ($MgSO_4$), the solvent was removed under reduced pressure and the residual oil crystallised from ether-pentane at $-10°$ to yield the (4R)-ester (13; $R^2=(CH_2)_6CO_2Me$, $R^3=H$) (21 mg) as rhombs, m.p. 56°-59°. Preparative layer chromatography of the mother liquors on silica gel in methylene dichlorideme-thanol (10:1), followed by crystallisation from ether-pentane, gave further (4R)-ester (13; $R^2=(CH_2)_6CO_2Me$, $R^3=H$)(5 mg; total yield 26 mg, 88%), $[\alpha]_{345}^{25}-1560°$ (c $4.14\times10$, MeOH), $[\alpha]_{237}^{25}+14,240°$ (c $4.14\times10^{-3}$, MeOH), $[\theta]_{320}^{25}-9858°$ (c $4.14\times10^{-2}$, MeOH), $[\theta]_{224}^{25}+64730°$ (c $4.14\times10^{-3}$, MeOH), with spectroscopic properties in agreement with literature data (Found: C, 65.3; H, 8.6. $C_{13}H_{20}O_4$ requires C,65.0; H, 8.4%). (* This compound is named here as a substituted ketone rather than as a substituted ester, so as not to obscure the description).

EXAMPLE 12

(1S,4S)-3,5,5-Trichloro-1,4-dihydroxycyclopent-2-ene-1-carboxylic acid (5)

After crystallisation of the ($-$)-brucine salt of the acid (4) in Example 1, gradual reduction in the volume of methanol produced several crops of dextrorotatory ($-$)-brucine salt (total 13.04 g). Several recrystallisations from ethanol gave the pure ($-$)-brucine salt of acid (5) (9.58 g, 74%) as colourless needles, m.p. 149°-152° (dec.), $[\alpha]_D^{25}+93°$ (c. 0.265, CHCl$_3$) (Found: C, 54.35; H, 5.25; Cl, 16.35; N, 4.1. $C_{29}H_{31}Cl_3N_2O_8$ requires C, 54.25; H, 4.85; Cl, 16.55; N, 4.35%).

Acidification of the salt (4.45 g) gave the (1S,4S)-acid(5) (1.70 g, 99%) as colourless rhombs from ether-light petroleum (b.p. 40°-60°) m.p. 188°-189°, $[\alpha]_D^{25}+207°$ (c 0.110, EtOH), $[\alpha]_{232}^{25}+15,420°$ (c $4.93\times10^{-3}$, EtOH), $[\theta]_{219}^{25}+76,310$ (c $4.93\times10^{-3}$, EtOH) (Found: C,29.5; H, 2.15; Cl, 42.95. $C_6H_5Cl_3O_4$ requires C, 29.1; H, 2.05; Cl, 43.0%).

EXAMPLE 13

(4S)-3,5,5-Trichloro-4-hydroxycyclopent-2-en-1-one (15)

Obtained by a process analogous to Example 2 from the (1S,4S)-acid as a colourless oil after short path distillation bath temp. 50°/0.05 mm Hg), $[\alpha]_{357}^{25}-1610°$ (c $5.05\times10^{-2}$, EtOH), $[\alpha]_{252}^{25}+14,600°$ (c $2.02\times10^{-3}$, EtOh), $[\theta]_{333}^{25}-8940$(c$5.05\times10^{-2}$, EtOH), $[\theta]_{240}^{25}+46,600$ (c $2.02\times10^{-3}$, EtOH) (Found: C, 29.7; H, 1.8; Cl, 51.7. $C_5H_3Cl_3O_2$ requires C, 29.8; H, 1.5; Cl, 52.8%).

EXAMPLE 14

(4R)-3-chloro-4-(dimethyl-t-butylsilyloxy)-cyclopent-2-en-1-one (17; $R^1=Me_2$, Bu$^t$Si)

Obtained by a process analogous to Example 3 from the (4S)-trichloro-enone (15) as a colourless oil, $[\alpha]_{352}^{25}-1050°$ (c $3.15\times10^{-2}$, hexane), $[\alpha]_{234}^{25}+17,290°$ (c $1.58\times10^{-3}$, hexane), $[\theta]_{333}^{25}-6770$ (c $3.15\times10^{-2}$, hexane) $[\theta]_{225}^{25}+83,780$ (c $1.58\times10^{-3}$ hexane) (Found: C, 53,8; H, 7.8; Cl, 14.5. $C_{11}H_{19}ClO_2Si$ requires C, 53.55; H, 7.75; Cl, 14.35%).

EXAMPLE 15

(4S)-4-(Dimethyl-t-butylsilyloxy)-3-[7-(tetrahydropyran-2-yloxy) heptyl]-cyclopent-2-en-1-one (9; $R^1=Me_2Bu^tSi$, $R^2=(CH_2)_7OThp$)

A suspension of cuprous iodide (76 mg, 0.4 mmol) in tetrahydrofuran (2 ml) containing the (4S)-enone (8; $R^1=Me_2Bu^tSi$) (100 mg, 0.4 mmol) was stirred vigorously at $-10°$ under argon. Dropwise addition of 7-(tetrahydropyran-2-xyloxy) heptyl magnesium bromide in tetrahydrofuran (0.47M, 1.62 ml, 0.76 mmol) produced a green solution which was stirred at $-10°$ for 10 min. The reaction was rapidly quenched with saturated aqueous ammonium chloride (5 ml), and after the addition of ether (5 ml) the mixture was stirred at room temperature for 1 hr., before dilution with water (10 ml) and extraction with ether (5×10 ml). The combined extracts were washed with brine (2×5 ml) dried (MgSo4) and evaporated. Purification by preparative layer chromatography on silica gel in methylene dichloride-methanol (50:1) gave the (4S)-enone (9; $R^1=Me_2Bu^tSi$, $R^2=(CH_2)_7OThp$) (135 mg, 83%) as a colourless oil, $[\alpha]_{362}^{25}+795°$; $[\alpha]_{345}^{25}+795°$ (c $1.825\times10^{-2}$, hexane), $[\alpha]_{228}^{25}-11,200°$ (c. $1.825\times10^{-3}$ hexane), $[\theta]_{324}^{25}+8670$ (c $1.825\times10^{-2}$, hexane), $[\theta]_{217}^{25}-96,150$ (c $1.825\times10^{-3}$, hexane) (Found: C, 67.5; H, 10.25. $C_{23}H_{42}SiO_4$ requires C, 67.25; H, 10.3%).

EXAMPLE 16

(1R, 4S)-4-(Dimethyl-t-butylsilyloxy)-3-[7-(tetrahydropyran-2-yloxy) heptyl]-cyclopent-2-en-1-ol (10; $R^1=Me_2Bu^tSi$, $R^2=(CH_2)_7OThp$)

Lithium tri-s-butylborohydride in tetrahydrofuran (lM, 0.508 ml, 0.508 mmol) was added dropwise with vigorous stirring to the (4S)-enone (9; $R^1=Me_2Bu^tSi$; $R^2=(CH_2)_7OThp$) (180 mg, 0.44 mmol) in tetrahydrofuran (3 ml) at $-78°$. After 1 hr. at this temperature, water (1 ml) was added and the mixture allowed to warm to room temperature. Dilution with water (10 ml) and extraction with ether (4×10 ml) gave, after drying (MgSo4) and evaporation of the extracts a pale yellow oil (264 mg). Preparative layer chromatography on silica gel in methylene dichloride-methanol (50:1) yielded the (1R, 4S)-alcohol (10; $R^1=Me_2Bu^tSi$, $R^2=(CH_2)_7OThp$) (145 mg, 80%) as a colourless oil (Found: C, 66.65; H. 10.4. $C_{23}H_{44}O_4Si$ requires C, 66.95; H, 10.75%).

EXAMPLE 17

(1S,4R)-1-(Dimethyl-t-butylsilyloxy)-2-[7-(tetrahydroxypuran-2-xyloxy) heptyl]-4-(tetrahydropyran-2-yloxy) cyclopent-2-ene (11; $R^1=Me_2Bu^tSi$, $R^2=(CH_2)_7OThp$, $R^3=Thp$)

Dihydropyran (21.3 mg, 0.25 mmol) was added dropwise to the (1R, 4S)-alcohol (10; $R^1=Me_2Bu^tSi$, $R^2=(CH_2)_7OThp$ (60 mg, 0.145 mmol) in methylene dichloride (1.5 ml) containing pyridinium p-toluene sulphonate (4 mg, 0.02 mmol). After 3h at room temperature the solution was diluted with ether (10 ml) washed with half-saturated brine (2×10 ml), dried (MgSO4) and evaporated. Preparative layer chromatography of the residue (81 mg) on silica gel in methylene dichloride methanol (50:1) gave the (1S, 4R)-diol derivative (11; $R^1=Me_2Bu^tSi$, $R^2=(CH_2)_7OThp$, $R^3=Thp$ (66 mg, 92%) as a colourless oil (Found: C,68.3; H, 10.8. $C_{28}H_{52}O_5Si$ requires C, 67.7; H, 10.55%.

EXAMPLE 18

(1S,4R)-2-[7-(Tetrahydropyran-2-yloxy)heptyl]-4-(tetrahydropyran-2-yloxy)cyclopent-2-en-1-ol(12; $R^2=(CH_2)_7OThp$, $R^3=Thp$)

To the (1S, 4R)-diol derivative (11; $R^1=Me_2Bu^tSi$, $R^2=(CH_2)_7OThp$, $R^3=Thp$) (174 mg, 0.35 mmol) in tetrahydrofuran (3 ml) at 0° was added dropwise tetrabutylammonium fluoride in tetrahydrofuran (0.4M, 1.75 ml). After 5.5 h at 0° the solution was diluted with water (5 ml) and extracted with ether (3×10 ml). The combined extracts were washed with saturated brine (2×5 ml), dried (MgSO4), and evaporated. Chromatography (p.l. c.) of the residual oil (240 mg) on silica gel in methylene dichloride-methanol (50:1) gave the (1S, 4R)-cyclopentenol (12; $R^2=(CH_2)_7OThp$, $R^3=Thp$) (122 mg, 91%) as a colourless oil (Found: C. 69.30; H, 10.2, $C_{22}H_{38}O_5$ requires C, 69.05; H, 10.0%).

EXAMPLE 19

(4R)-2-[7-(tetrahydropyran-2-yloxy)heptyl]-4-(tetrahydropyran-2-yloxy)cyclopent-2-en-1-one (13; $R^2(CH_2)_7OThp$ $R^3=Thp$)

Pyridinium chlorochromate (110 mg, 0.51 mmol) was added in one portion to a suspension of anhydrous sodium acetate (8 mg, 0.1 mmol) in methylene dichloride (2 ml) containing the (1S,4R)-cyclopentenol (12; $R^2=(CH_2)_7OThp$, $R^3=Thp$)(122 mg, 0.32 mmol).

After stirring at room temperature for 2 h the mixture was diluted with ether (10 ml) and the reduced reagent was removed by filtration through a pad of "Florisil". Evaporation of the solvent under reduced pressure and chromatographic purification of the residual oil (133 mg) on silica gel in methylene-dichloridemethanol (50:1) gave the (4R)-cyclopentenone (13; $R^2=(CH_2)_7Othp$, $R^3=Thp$)(117 mg, 96%) as a colourless oil, $[\alpha]_{342}^{25}-1140°$ )C $2.625\times10^{-2}$, MeOH), $[\alpha]_{238}^{25}+10,285°$ (c $0.525\times10^{-2}$, MeOH), $[\theta]_{318}^{25}-10,510$ (c $2.625\times10^{-2}$, MeOH), $[\theta]_{227}^{25}+73,930$ (c $0.525\times10^{-3}$, MeOH) (Found: C, 70.05; H, 9.55. $C_{22}H_{36}O_5$ requires C, 69.45; H, 9.55%).

EXAMPLE 20

(4R)-2-(7-Hydroxyheptyl)-4-hydroxycyclopent-2-en-1-one (13; $R^2=(CH_2)_7OH$, $R^3=H$)

The (4R)-bis-tetrahydropyran-2-yl ether (13; $R^2(CH_2)_7OThp$, $R^3=Thp$)(100 mg, 0.263 mmol) in aqueous acetic acid (80%, 1ml) containing a trace of tetrahydrofuran was maintained at room temperature for 48 h. Solvent was removed under reduced pressure and the residue was purified by preparative layer chromatography on silica gel in methylene dichloridemethanol (20:1) to yield the (4R)-cyclopentenone (13; $R^2=(CH_2)_7OH$, $R^3=H$) (54 mg, 98%) as colourless needles from chloroform-light petroleum (b.p. 60°-80°), m.p. 63°-65° $[\alpha]_{345}^{25}-1845$ (c $3.58\times10^{-2}$, MeoH), $[\alpha]_{238}^{25}+17,320°$ (c. $3.58\times10^{-3}$, MeOH), $[\theta]_{316}^{25}-8660$ (c $3.58\times10^{-2}$, MeOH) $[\theta]_{222}^{25}+49,810$ (c $3.58\times10^{-3}$, MeOH) (Found: C, 67.95; H, 9.4. $C_{12}H_{20}O_3$ requires C, 67.9; H 9.5%.)

EXAMPLE 21

(4RS)-4-(Dimethyl-t-butylsilyloxy)-3-(7-hydroxyheptyl) cyclopent-2-en-1-one((±)-9; $R^1$=Me$_2$Bu$^t$Si, $R^2$=(CH$_2$)$_7$OH)

(4RS)-4-(Dimethyl-t-butylsilyloxy)-3-[7-(dimethyl-t-butylsilyloxy)heptyl]-cyclopent-2-en-1-one ((±)-9; $R^1$=Me$_2$Bu$^t$Si, $R^2$=(CH$_2$)$_7$OSiMe$_2$Bu$^t$) (69 mg, 0.156 mmol) in acetic acid-tetrahydrofuran-water (3:1:1, 0.5 ml) was maintained at room temperature for 17 h. Removal of the solvent under reduced pressure and preparative layer chromatography of the residual oil on silica gel in methylene dichloride-methanol (20:1) afforded the primary alcohol ( (±)-9; $R^1$=Me$_2$Bu$^t$Si, $R^2$=(CH$_2$)$_7$OH)(46 mg, 90%) as a colourless oil (Found: C, 66.6; H, 10.4. C$_{18}$H$_{34}$O$_3$Si requires C, 66.2; H, 10.5%).

EXAMPLE 22

(4RS)-3-(6-Carboxyhexyl)-4-(dimethyl-t-butylsilyloxy) cyclopent-2-en-1-one ( (±) -9; $R^1$=Me$_2$Bu$^t$Si, $R^2$=(CH$_2$)$_6$CO$_2$H).

Jones reagent was added over 3 h to the primary alcohol ((±)-9; $R^1$=Me$_2$Bu$^t$Si, $R^2$=(CH$_2$)$_7$OH (175 mg, 0.536 mmol) in acetone (10 ml) at $-10°$ so that an excess of oxidant was maintained. After this time, isopropanol was added to destroy excess of oxidant. The solution was diluted with water (20 ml), extracted with ether (5×15 ml), and the combined extracts were washed with saturated brine (2×5 ml), dried (MgSO$_4$) and evaporated under reduced pressure. The oily carboxylic acid ( (±)-9; $R^1$=Me$_2$Bu$^t$Si, $R^2$=(CH$_2$)$_6$CO$_2$H) (165 mg, 90%) obtained was homogenous by thin layer chromatography and was employed without further purification.

EXAMPLE 23

(4RS)-4-(Dimethyl-t-butylsilyloxy)-3-(6-ethoxycarbonylhexyl) cyclopent-2-en-1-one( (±)-9; $R^1$=Me$_2$Bu$^t$Si, $R^2$=(CH$_2$)$_6$ CO$_2$Et)

A solution of 1,5-diazabicyclo[5.4.0]undec5-ene (DBU, 73.6 mg 0.484 mmol) in benzene (0.5 ml) was added with stirring to the chromatographyically pure acid ( (±)-9; $R^1$=Me$_2$Bu$^t$Si, $R^2$=(CH$_2$)$_6$CO$_2$H) (165 mg, 0.484 mmol) and ethyl iodide (75.5 mg, 0.484 mmol) in benzene (1.5 ml) at room temperature. After 18 h the mixture was filtered and the filtrate was evaporated under reduced pressure to yield a pale yellow oil. Chromatographic purification on silica gel in methylene dichloride-methanol (20:1) gave the ester ((±)-9; $R^1$=Me$_2$Bu$^t$Si, $R^2$=(CH$_2$)$_6$CO$_2$Et) (147 mg, 96% based on acid consumed) as a colourless oil (Found: C, 65.35; H, 9.75. C$_{20}$H$_{36}$O$_4$Si requires C, 65.15; H, 9.85%).

EXAMPLE 24

(1R*, 4S*)-4-(Dimethyl-t-butylsilyloxy)-3-(6-ethoxy-carbonyl-hexyl) cyclopent-2-en-1-ol ((±)-10; $R^1$=Me$_2$Bu$^t$Si; $R^2$=(CH$_2$)$_6$CO$_2$Et).

Lithium tri-s-butylborohydride in tetrahydrofuran (1M, 0.150 ml, 0.150 mmol) was added dropwise with vigorous stirring to the enone ((±)-9; $R^1$=Me$_2$Bu$^t$Si, $R^2$=(CH$_2$)$_6$CO$_2$Et)(50 mg, 0.136 mmol) in tetrahydrofuran (1ml) at $-78°$. After 0.5 h at this temperature water (0.5 ml) was added and the mixture allowed to warm to room temperature. Dilution with water (5 ml) and extraction with ether (4×5 ml) gave, after drying (MgSO$_4$) and evaporation of the combined extracts, a pale yellow oil (60 mg). Preparative layer chromatography on silica gel in methylene dichloride-methanol (20:1) yielded the (1R*, 4S*)-alcohol ((±)-10; $R^1$=Me$_2$Bu$^t$Si, $R^2$=(CH$_2$)$_6$ CO$_2$Et) (47 mg, 93%) as a colourless oil (Found: C, 65.1; H, 10.2. C$_{20}$H$_{38}$O$_4$Si requires C, 64.8; H, 10.35%).

EXAMPLE 25

(1S*, 4R*)-1-(Dimethyl-t-butylsilyloxy)-2-(6-ethoxycarbonyl-hexyl)-4-(tetrahydropyran-2-yloxy)cyclopent-2-ene ((±)-11; $R^1$=Me$_2$Bu$^t$Si; $R^2$=(CH$_2$) $_6$CO$_2$Et$_\mu$, $R^3$=Thp)

Dihydropyran (16.8 mg, 0.2 mmol) was added dropwise to the (1R*, 4S*)-alcohol ((±)-10; $R^1$=Me$_2$Bu$^t$Si; $R^2$=(CH$_2$)$_6$CO$_2$Et) (50 mg, 0.135 mmol) in methylene dichloride (1 ml) containing pyridinium p-toluenesulphonate (3 mg, 0.015 mmol). After 4 h at room temperature the solution was diluted with ether (10 ml), washed with half-saturated brine (10 ml), dried (MgSO$_4$) and evaporated. Preparative layer chromatography of the residue (74 mg) on silica gel in methylene dichloride-methanol (50:1) gave the (1S*, 4R*)-diol derivative ((±)-11; $R^1$=Me$_2$Bu$^t$Si, $R^2$ =(CH$_2$)$_6$CO$_2$Et, $R^3$=Thp)(61 mg, 100%) as a colourless oil (Found: C, 66.15; H, 10.15. C$_{25}$H$_{46}$O$_5$Si requires C, 66.05; H, 10.2%.

EXAMPLE 26

(1S*, 4R*)-2-(6-Ethoxycarbonylhexyl)-4-(tetrahydropyranyloxy) cyclopent-2-en-1-ol ((±)-12; $R^2$=(CH$_2$)$_6$CO$_2$Et. $R^3$=Thp)

To the (1S*, 4R*)-diol derivative ((±)-11; $R^1$=Me$_2$Bu$^t$Si, $R^2$=(CH$_2$)$_6$CO$_2$Et, $R^3$=Thp)(55 mg, 0.12 mmol) in tetrahydrofuran (1 ml) at 0° was added dropwise tetrabutylammonium fluoride in tetrahydrofuran (0.4M, 0.6 ml). After 5.5 h at 0° the solution was diluted with water (5 ml) and extracted with ether (3×10 ml). The combined extracts were washed with saturated brine (2×5 ml), dried (MgSO$_4$) and evaporated. Chromatographic purification of the residue (55 mg) on silica gel in methylene dichloride-methanol (20:1) gave the (1S*,4R*)-cyclopentenol ((±)-12; $R^2$=(CH$_2$)$_6$CO$_2$Et, $R^3$=Thp)(37 mg, 90%) as a colourless oil (Found: C, 67.35; H, 9.35, C$_{19}$H$_{32}$O$_5$ requires C, 67.05; H, 9.5%.)

EXAMPLE 27

(4RS)-2-(6-Ethoxycarbonylhexyl)-4-(tetrahydropyran-2-yloxy) cyclopent-2-en-1-one((±)-13; $R^2$=(CH$_2$)$_6$CO$_2$Et, $R^3$=Thp)

Pyridinium chlorochromate (24mg, 0.11 mmol) was added to a suspension of anhydrous sodium acetate (2mg, 0.025 mmol) in methylene dichloride (1ml) containing the (1S*, 4R*)-alcohol (±)-12; $R^2$=(CH$_2$)$_6$CO$_2$ Et, $R^3$=Thp)(23 mg, 0.067 mmol).

After stirring at room temperature for 2 h the mixture was diluted with ether (3 ml) and filtered through a pad of "Florisil". Evaporation of the filtrate under reduced pressure and chromatographic purification of the residual oil on silica gel in methylene dichloride - methanol (100:5) gave the ester ((±)-13; $R^2$=(CHO$_2$)$_6$C$_2$Et, $R^3$=Thp)(21 mg, 93%) as a colourless oil (Found : C, 67.3; H, 8.8. C$_{19}$H$_{30}$O$_5$ requires C, 67.45; H, 8.95%).

EXAMPLE 28

(4RS)-2-(6-Ethoxycarbonylhexyl)-4-hydroxycyclopent-2-en-1-one (($\pm$)-13; $R^2=(CH_2)_6CO_2Et$, $R^3=H$)

The ester (($\pm$)-13, $R^2=(CH_2)_6CO_2Et$, $R^3=Thp$) (70 mg, 0.21 mmol) in acetic acid-tetrahydrofuran-water (3:1:1:, 2 ml) was maintained at room temperature for 24 h. Solvent was removed under reduced pressure and the residue was purified by preparative layer chromatography on silica gel in methylene dichloride-methanol (10:1) to yield the hydroxy-enone (($\pm$)-13; $R^2=(CH_{26}CO_2Et$, $R^3=H$) (53 mg, 99%) as a colourless oil (Found : C, 66.1; H, 8.7. $C_{14}H_{22}O_4$ requires C, 66.1; H, 8.7%).

EXAMPLE 29

(4RS)-3-butyl-4-(dimethyl-t-butylsilyloxy)cyclopent-2-en-1-one (($\pm$)-9; $R^1=Me_2Bu^tSi$, $R^2=Bu$)

(a) From Chloro-enone (($\pm$)-8; $R^1=Me_2Bu^tSi$) and Lithium n-Butyl(phenylthio) copper (I).n-Butyllithium in hexane (1.6 M, 0.32 ml, 0.51 mmol) was added dropwise to a vigorously stirred suspension of phenylthiocopper (I) (88 mg, 0.51 mmol) in tetrahydrofuran (5 ml) at $-20°$ under argon. After 10 min at this temperature the pale yellow solution was cooled to $-78°$ and the chloro-enone (($\pm$)-8; $R^1=Me_2Bu^tSi$) (85 mg, 0.34 mmol) in tetrahydrofuran (1 ml) was added dropwise. The mixture was allowed to warm to $-20°$ over 1 h and after a further 1.5 h at this temperature the mixture was poured rapidly into saturated aqueous ammonium chloride solution (10 ml) and covered by a layer of ether (20 ml). After stirring overnight the layers were separated and the blue aqueous phase was extracted with ether (3$\times$10 ml). The ether extracts were combined, washed successively with ammonium chloride solution (10 ml) and saturated brine (2$\times$10 ml), and then dried (MgSO$_4$) Removal of the solvent under reduced pressure and chromatography of the residue on silica gel in methylene dichloride-methanol (50:1) gave the enone ($\pm$)-9; $R^1=Me_2Bu^tSi$, $R^2=Bu$) (67 mg, 74%) as a colourless liquid (Found: C, 67.25; H, 10.3. $C_{15}H_{28}O_2Si$ requires C, 67.1; H, 10.5%).

(b) From Chloro-enone ($\pm$)-8; $R^1=Me_2Bu^tSi$) and Butylmagnesium Bromide

A suspension of cuprous iodide (68.5 mg, 0.36 mmol) in tetrahydrofuran (2 ml) containing the chloroenone (($\pm$)-8; $R^1=Me_2Bu^tSi$) (88 mg, 0.36 mmol) was stirred vigorously at 0° under argon. Dropwise addition of n-butyl magnesium bromide in tetrahydrofuran (0.72 M, ml, 0.72 mmol) produced a yellow-green solution which changed to deep-green over 1 h at 0°. After this time the reaction was rapidly quenched with saturated aqueous ammonium chloride (5 ml), and after the addition of ether (5 ml) the mixture was stirred at room temperature for 1 h before dilution with water (10 ml) and extraction with ether (5$\times$10 ml). The combined extracts were washed with brine (2$\times$5 ml), dried (MgSO$_4$),and evaporated. The residual oil (126 mg) was purified as in (a) to give the enone (($\pm$)-9; $R^1=Me_2Bu^tSi$, $R^2=Bu$) (90 mg, 94%) identical with that described above.

EXAMPLE 30

2(1R*,4S*)-3-Butyl-4-(dimethyl-t-butylsilyloxy)cyclopent-2-en-1-ol ($\pm$)-10; $R^1=Me_2Bu^tSi$, $R^2=Bu$)

Lithium tri-s-butylborohydride in tetrahydrofuran (1 M, 0.5 ml, 0.5 mmol) was added dropwise with vigorous stirring to the enone (($\pm$)-9; $R^1=Me_2Bu^tSi$, $R^2=Bu$) (60 mg, 0.223 mmol) in tetrahydrofuran (0. 5 ml) at $-78°$. After 2 h at this temperature water (1 ml) was added and the mixture allowed to warm to room temperature. Dilution with water (5 ml) and extraction with ether (5 $\times$8 ml) gave, after drying (MgSO$_4$) and evaporation of the extracts, a colourless oil (155 mg). Preparative layer chromatography on silica gel in methylene dichloridemethanol (50:1) yielded the (1R*,4S*)-alcohol (($\pm$)-10; $R^1=Me_2Bu^tSi$, $R^2=Bu$) (56 mg, 93%) as a colourless oil (Found: C, 66.7; H, 11.3. $C_{15}H_{30}O_2Si$ requires C, 66.6; H, 11.2%).

EXAMPLE 31

(1S*,4R*)-2-Butyl-1-(dimethyl-t-butylsilyloxy)-4-(tetrahydropyran -2-yloxy)cyclopent-2-ene (($\pm$)-11; $R^1=Me_2Bu^tSi$, $R^2=Bu$, $R^3=Thp$)

Dihydropyran (16.8 mg, 0.2 mmol) was added dropwise to the (1R*,4S*)-alcohol (($\pm$)-10; $R^1=Me_2Bu^tSi$, $R^2=Bu$) (40 mg, 0.15 mmol) in methylene dichloride (1 ml) containing p-toluenesulphonic acid (0.01 M) at 0°. After 3 h the solution was diluted with ether (10 ml), washed successively with 5% aqueous sodium bicarbonate (5 ml) and water (2$\times$5 ml), and dried (MgSO$_4$). Removal of the solvent under reduced pressure and chromatography of the residue (46 mg) on a column of silica gel (10 g) in methylene dichloride-methanol (50:1) gave the (1S*,4R*)diol derivative ($\pm$)-11; $R^1=Me_2Bu^tSi$, $R^2=Bu$, $R^3=Thp$) (39 mg, 73%) as a colourless liquid (Found: C, 67.6; H, 10.85. requires $C_{20}H_{38}O_3Si$, 67.75; H, 10.8%).

EXAMPLE 32

(1S*,4R*)-2-Butyl-4-(tetrahydropyran-2-yloxy) cyclopent-2-en-1-ol (($\pm$)-12; $R^2=Bu$, $R^3=Thp$)

To the (1S*,4R*)-diol derivative (($\pm$)-11; $R^1=Me_2Bu^tSi$, $R^2=Bu$, $R^3=Thp$)(24 mg, 0.068 mmol) in tetrahydrofuran (0.5 ml) at 0° was added slowly tetrabutylammonium butylammonium fluoride in tetrahydrofuran (0.5 M, 0.27 ml). After 2 h at 0° the solution was diluted with water (5 ml) and extracted with ether (3$\times$15 ml). The combined extracts were dried (MgSO$_4$), evaporated and the residual oil (40 mg) was chromatographed on a column of silica gel (5 g) in light petroleum (b.p. 60°-80°)-ether (1:1) to give the (1S*,4R*)-alcohol (($\pm$)-12; $R^2=Bu$, $R^3=Thp$) (14 mg, 88%) as a colourless oil (Found: C, 69.65; H, 10.2. $C_{14}H_{24}O_3$ requires C, 69.95; H, 10.05%).

EXAMPLE 33

(4RS)-2-Butyl-4-(tetrahydropyran-2-yloxy) cyclopent-2-en-1-one (($\pm$)-13; $R^2=Bu$, $R^3=Thp$)

Pyridinium chlorochromate (12.9 mg, 0.06 mmol) was added to a suspension of anhydrous sodium acetate (1 mg, 0.012 mmol) in methylene dichloride(0.3 ml) containing the (1S*,4R*)-alcohol ($\pm$)-12; $R^2=Bu$, $R^3=Thp$) (8 mg, 0.033 mmol). After stirring at room temperature for 2 h the mixture was diluted with ether (1 ml) and filtered through a pad of "Celite". Evaporation of the filtrate under reduced pressure and chromatographic purification of the residual oil (10 mg) on silica gel (p.l.c.) in methylene dichloride-methanol (50:1) gave the enone ($\pm$)-13; $R^2=Bu$, $R^3=Thp$) (6.6 mg, 83%) as a colourless oil (Found: C, 70.55; H, 9.2. $C_{14}H_{22}O_3$ requires c, 70.55; H, 9.3%).

EXAMPLE 34

(1S*,4S*)-4-Benzoyloxy-1-(dimethyl-t-butylsilyloxy) -2-(6-ethoxycarbonylhexyl)cyclopent-2-ene (($\pm$)-20; $R^1=Me_2Bu^tSi$, $R^2=$, $(CH_2)_6CO_2Et$, $R^3=COPh$)

The (1R*,4S*)-alcohol ((+)-19; $R^1=Me_2Bu^tSi$, $R^2=(CH_2)_6CO_2Et$) (37 mg, 0.1 mmol), diethyl azodicarboxylate (34.8 mg, 0.2 mmol), triphenyl phosphine (52.5 mg, 0.2 mmol) and benzoic acid (24.4 mg, 0.2 mmol) were stirred together in tetrahydrofuran (1 ml) for 20 h. Evaporation of the solvent under reduced pressure gave a semicrystalline residue which was triturated with ether. Filtration, removal of solvent from the filtrate and preparative layer chromatography of the residual oil on silica gel in methylene dichloride (100%) gave the (1S*,4S*)-benzoate (($\pm$)20; $R^12$ Med $2Bu^tSi$, $R^2=(CH_2)_6CO_2Et$, $R^3=COPh$) (44 mg, 93%) as a colourless oil (Found: C, 68.6; H, 8.55. requires $C_{27}H_{42}O_5Si$, 68.3; H, 8.9%).

EXAMPLE 35

(1S*,4S*)-4-(Dimethyl-t-buylsilyloxy)-2-(6-methoxycarbonylhexyl) cyclopent-2-en-1-ol (($\pm$)-20; $R^1=Me_2Bu^tSi$, $R^2=$, $(CH_2)_6CO_2Me$, $R^3=H$)

To the (1S*,4S*)-benzoate (($\pm$)-20; $R^1=Me_2Bu^tSi$, $R^2=(CH_2)_6CO_2Et$, $R^3=CoPh$)(32 mg, 0.067 mmol) in methanol (2 ml) was added aqueous potassium carbonate (2%, 0.5 ml) and the mixture was stirred at room temperature. After 24 h solvent was removed under reduced pressure and the residue was partitioned between water (5 ml) and ether (10 ml). The aqueous phase was extracted with three further portions of ether (5 ml) and the combined ether extracts were washed with water (2×5 ml) before drying (MgSO4). Preparative layer chromatography of the residual oil (32 mg) on silica gel in methylene dichloride-methanol (50:1) gave the (1S*,4S*)-alcohol (($\pm$)-20; $R^1=Me_2Bu^tSi$, $R^2=(CH_2)_6CO_2Me$, $R^3=H$) (17 mg, 75%) as a colourless oil (Found: c, 64.15; H, 10.15. $C_{19}H_{36}O_4Si$ requires C, 64.0; H, 10.2%).

EXAMPLE 36

(1S*,4S*)-4-Benzoyloxy-1-(dimethyl-t-butylsilyloxy) -2-[7-(dimethyl-t-butysilyoxy)heptyl]cyclopent-2-ene(($\pm$)-20; $R^1=Me_2Bu^tSi$, $R^2=(CH_2)_7OSiMe_2Bu^t$, $R^3=COPh$)

The (1R*,4S*)-alcohol (($\pm$)-19; $R^1=Me_2Bu^tSi$, $R^2=(CH_2)_7OSiMe_2Bu^t$) (100 mg, 0.226 mmol), diethyl azodicarboxylate (71 ml, 0.45 mmol), triphenylphosphine (118 mg, 0.45 mmol) and benzoic acid (55 mg, 0.45 mmol) were stirred together in tetrahydrofuran (2 ml) for 20 h. Removal of the solvent and trituration of the residue with ether gave a crystalline residue which was removed by filtration. Evaporation of the filtrate and preparative layer chromatography of the residue (425 mg) on silica gel in methylene dichloride gave the (1S*,4S*)-benzoate (($\pm$)-20; $R^1=Me_2Bu^tSi$, $R^2=(CH_2)_7OSiMe_2Bu^t$, $R^3=COPh$) (112 mg, 91%) as a colourless oil (Found: c, 68.25; H, 9.85. $C_{31}H_{54}O_4Si_2$ requires C, 68.05; H, 9.95%).

EXAMPLE 37

(1S*,4S*)-4-(Dimethyl-t-butylsilyloxy)-2-[7-(dimethyl-t-butylsilyoxy) heptyl]cyclopent-2-en-1-ol (($\pm$)-20; $R^1=Me_2Bu^tSi$, $R^2=(CH_2)_7$ $OSiMe_2Bu^t$, $R^3=H$).

The (1S*,4S*) benzoate (($\pm$)-20; $R^1=Me_2Bu^tSi$, $R^2=(CH_2)_7OSiMe_2Bu^t$, $R^3=COPh$) (48 mg, 0.0877 mmol) was stirred with potassium carbonate (100 mg) in methanol (5 ml) for 4 h. After removal of the solvent under reduced pressure the residue was extracted with ether (4×5 ml) and the combined extracts were washed with water (2×5 ml), dried MgSO4 and evaporated to yield the (1S*,4S*)-alcohol (($\pm$)-20; $R^1=Me_2Bu^tSi$, $R^2=(CH_2)_7OSiMe_2Bu^t$, $R^3=H$) (36 mg, 93%) as a chromatographically and spectroscopically pure oil (Found: M+·442; M+-H2O, 424.3197. $C_{24}H_{48}O_2Si_2$ requires M+, 442; M+-H2O, 424.3193).

We claim:

1. A compound of the general formula I:

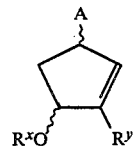

wherein A represents H, $OR^z$; $R^z$ represents hydrogen or a removable alcohol protecting group selected from the group consisting of substituted silyl, alkoxyalkyl, tetrahydrofuran-2-yl and tetrahydropyran-2-yl; $R^x$ represents hydrogen or a removable alcohol protecting group as defined above; with the proviso that $R^x$ and $R^z$ are not the same and that when each of $R^x$ and $R^z$ represents a removable alcohol protecting group, $R^x$ is capable of being selectively removed without reomoval of $R^z$; and $R^y$ represents a group of the formula $R^2$, and $R^2$ represents a straight- or branched-chain alkyl, alkenyl or alkynyl group which may optionally be substituted by one or more carboxyl, carboxylic acid ester, or free or protected hydroxy, thiol, aldehyde or keto groups; wherein the protected groups are selected from lower alkyl ethers and thio ethers, hydroxyl groups protected with substituted silyl, alkoxyalkyl, tetrahydrofuran-2-yl or tetrahydropyran-2-yl group, noncyclic or cyclic acetals and ketals and their thio analogues.

2. A compound as claimed in claim 1, wherein $R^x$ represents a trisubstituted silyl gorup wherein said substituents are selected from the group consisting of alkyl, aryl and mixtures thereof.

3. A compound as claimed in claim 2, wherein $R^x$ represents a dimethyl-t-butyl silyl group.

4. A compound as claimed in claim 1 where said alkyl, alkenyl, or alkynyl group has up to 10 carbon atoms.

5. A compound as claimed in claim 4, wherein said alkyl, alkenyl or alkynyl group has from 4 to 10 carbon atoms.

6. A compound as claimed in claim 1, wherein said alkyl, alkenyl or alkynyl group is substituted by dimethyltbutylsilyloxy or tetrahydropyran-2-yloxy group.

7. A compound as claimed in claim 1, wherein $R^z$ represents an alkoxyalkyl group, a tetrahydrofuran-2-yl group or a tetrahydropyarn-2-yl group.

8. A compound as claimed in claim 7, wherein $R^z$ represents an ethoxyethyl group.

9. 4-(Dimethyl-t-butylsilyloxy)-3-cyclopent-2-en-1-ol.

10. 1-(Dimethyl-t-butylsilyloxy)-2-4-(tetrahydropyran-2-yloxy) cyclopent-2-ene.

11. 2-(7-Hydroxyheptyl)-4-(tetrahydropyran-2-yloxy) cyclopent-2-en-1-ol.

12. 4-(Dimethy-t-butylsilyloxy)-3-[7-(tetrahydropyran pyran-2-yloxy)heptyl]-cyclopent-2-en-1-ol.

13. 1-(Dimethyl-t-butylsilyloxy)-2-[7-(tetrahydropyran-2-yloxy) heptyl]-4-(tetrahydropyran-2-yloxy)cyclopent-2-ene.

14. 2-[7-(Tetrahydropyran-2-yloxy)heptyl]-4-(tetrahydropyran-2-yloxy) cyclopent-2-en-1-ol.

15. A process for the preparation of compounds of the general formula Ig:.

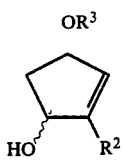

wherein $R^2$ is as defined in claim 1 and $R^3$ represents a removable alcohol protecting group selected from the group consisting of substituted silyl, alkoxyalkyl, tetrahydrofuran-2-yl and tetrahydropyran-2-yl, which comprises:

(a) reduction of a compound of the general formula Id:

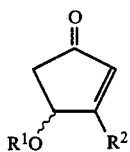

wherein $R^1$ represents a removable alcohol protecting group selected from the group consisting of substituted silyl, alkoxyalkyl, tetrahydrofuran-2-yl and tetrahydropyran-2-yl, with the proviso that $R^1$ and $R^3$ are not the same protecting group and $R^1$ is capable of being selectively removed without removal of $R^3$, and $R^2$ is as defined in claim 1, to produce a compound of the general formula Ie

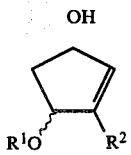

wherein $R^1$ and $R^2$ are defined above;

(b) protection of the free hydroxyl substituent of compound of the general formula If

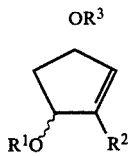

wherein $R^1$, $R^3$ and $R^2$ are as defined above and;

(C) selective removal of the $R^1$ protecting group of a compound of the general formula If as defined above to produce a compound of the gelneral formula Ig:

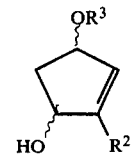

wherein $R^3$ and $R^2$ are as defined above.

16. A process as claimed in claim 15, further including the step of total or partial resolution of a racemic mixutre of the compound of the general formula Ie, if or Ig.

17. A process as claimed in claim 15, wherein said stereospecific reduction is carried out with a metal hydride.

18. A process as claimed in claim 17, wherein said metal hydride is lithium tri-s-butylborohydride.

19. A process as claimed in claim 15, wherein said step of protection of the free hydroxyl substituent is carried out by reaction of the compound of the general formula Ie with dihydrofuran or dihydropyran.

20. A process as claimed in claim 15, wherein said selective removal of a protecting group is carried out by displacement with fluoride anion.

21. A process as defined in claim 15, further including the step of total or partial inversion of the configuration of the hydroxy substituent in the formula Ie.

22. A process as defined in claim 15, further including the step of total or partial inversion of the configuration of the —$OR^3$ substituent of formula If.

23. A process as defined in claim 15, further including the step of total or partial inversion of the configuration of the —$OR^3$ substituent of formula Ig.

24. A compound of the general formula I:

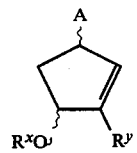

wherein A represents H, $OR^z$; $R^2$ represents hydrogen or a removable alcohol protecting group selected from the group consisting of alkoxyalkyl, tetrahydroguran-2-yl and tetrahydropyran-2-yl; $R^x$ represents hydrogen or a removable alcohol protecting group which is a silyl group tri-substitted with alkyl and/or aryl residues; with the provisio that $R^x$ and $R^z$ are not both hydrogen; and $R^y$ represents a group of the formula $R^2$, and $R^2$ represents a straight-or branched-chain alkyl, alkenyl or alkynyl group which may optionally be substituted by one or more carboxyl, carboxylic acid ester, or free or protecte hydroxy, thiol, aldehyde or keto groups, wherein the protected groups are selected from lower alkyl ethers and thio ethers, hydroxyl group protected with substituted silyl, alkoxyalkyl, tetraydrofuran-2-yl or tetrahydropyran-2-yl, non-cyclic or cyclic acetals and ketal and their thio analogues.

25. A process for preparation of compounds of the general formula Ig:

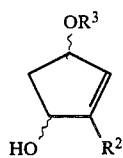

wherein $R^2$ is as defined in claim 24 and $R^3$ represnets a removable alcohol protecting group selected from the group consisting of alkoxylalkyl, tetrahydrofuran-2-yl and tetrahydropyran-2-yl; which comprises:

(a) reduction of a compound of the general formula Id:

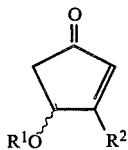

wherein $R^1$ represents a removable alcohol protecting group which is a silyl group tri-substituted with alkyl and/or aryl residues and $R^2$ is as defined above, to produce a compound of the general formula Ie:

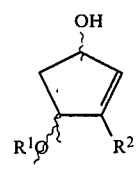

wherein $R^1$ and $R^2$ are as defined above;

(b) protection of the free hydroxyl substituent of a compound of the genral formula Ie as defined above to produce a compound of the gendral formula If:

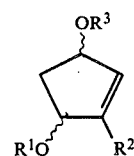

wherein $R^1$, $R^3$ and $R^2$ are as defined above;

(c) selective removal of the $R^1$ protecting group of a compound of the general formula If as defined above to produce a compound of the general formula Ig:

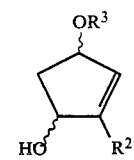

wherein $R^3$ and $R^2$ are as defined above.

* * * * *